United States Patent [19]

Turjanski et al.

[11] Patent Number: 5,779,713
[45] Date of Patent: Jul. 14, 1998

[54] INSTRUMENT FOR REMOVING NEUROLOGIC TUMORS

[76] Inventors: Leon Turjanski, Republica de la India 3129 (1425), Buenos Aires, Argentina; Carl E. Fabian, 577 NE. 96th St., Miami Shores, Fla. 33138

[21] Appl. No.: 697,425

[22] Filed: Aug. 23, 1996

Related U.S. Application Data

[63] Continuation of Ser. No. 254,861, Jun. 6, 1994, abandoned, which is a continuation-in-part of Ser. No. 72,717, Jun. 7, 1993, abandoned.

[51] Int. Cl.$^6$ ............................................. A61F 11/00
[52] U.S. Cl. ............................................. 606/108; 606/170
[58] Field of Search ............................................. 606/169–170, 606/108, 152; 128/92 R; 604/22; 15/23

[56] References Cited

U.S. PATENT DOCUMENTS

| | | | |
|---|---|---|---|
| 4,203,444 | 5/1980 | Bonnell et al. | 128/276 |
| 4,277,184 | 7/1981 | Solomon | 128/92 R |
| 4,504,264 | 3/1985 | Kelman | 604/22 |
| 4,798,586 | 1/1989 | Stevens | 604/96 |
| 4,883,045 | 11/1989 | Theisz | 604/25 X |
| 5,176,677 | 1/1993 | Wuchinich | 604/22 X |
| 5,307,534 | 5/1994 | Miller | 15/23 X |

*Primary Examiner*—Gary Jackson
*Assistant Examiner*—Nancy Mulcare
*Attorney, Agent, or Firm*—Ernest D. Buff

[57] ABSTRACT

Diseased tissue is liquefied in the presence of non-diseased tissue by contact with a paddle moving with angular velocity. The edge of the paddle is dull and the angular velocity is sufficient to batter the diseased tissue into a liquid without adversely affecting the structure and function of the non-diseased tissue. The shape of the paddle and the rotational speed can be designed and chosen depending on the consistency of the tissue to be resected, whether hard or soft. Upon liquefaction, the diseased tissue is removed by vacuum aspiration. This instrument therefore gives the neurosurgeon the ability to differentially resect diseased tissue while preserving the surrounding structures intact. The process is carried out using an inexpensive, maneuverable, small caliber instrument in a highly efficient manner

7 Claims, 9 Drawing Sheets

INSTRUMENT FOR REMOVING NEUROLOGIC TUMORS

CROSS-REFERENCE TO RELATED APPLICATIONS

This application is a continuation of application of Ser. No. 08/254,861 filed Jun. 6, 1994 now abandoned, which, in turn is a continuation-in-part of Ser. No. 08/072,717, filed Jun. 7, 1993, now abandoned.

BACKGROUND OF THE INVENTION

1. Field of the Invention

The present invention relates to an improved apparatus and process for the removal of tumors and other abnormal tissue from the central nervous system.

2. Description of the Prior Art

Neurosurgical operations are often performed for the purpose of removing tumors or abnormal tissue from the central nervous system. In the brain and spinal cord, access to abnormal tissue is usually restricted by the need to preserve surrounding or adjacent normal structures. Unlike abdominal surgery where incising and opening the abdominal wall results in a large operative cavity which usually allows access to the entire circumference of a tumor and enables it to be dissected free and removed en bloc, a neurosurgical procedure is more analogous to working through a keyhole. One must often traverse vital normal tissue to access the tumor and it is imperative to do as little collateral damage to the surrounding tissue as possible. It is therefore generally necessary to remove a tumor piecemeal, essentially chipping away at it and removing it bit by bit.

In an effort to facilitate the removal of tumors, various neurosurgical devices have been contrived which generally operate by macerating or liquefying the abnormal tissue, and then removing it by aspiration. For example, neurosurgeons sometimes use a device called a cavitron ultrasonic surgical aspirator (CUSA) to remove brain tumors in a more expeditious manner. These devices, hereinafter referred to as "Ultrasonic Devices", use magnetostrictive or piezoelectric technology to drive an operating head in a rapid, typically 23 kHz, to-and-fro motion causing disintegration of the tissue to be removed. See page 457 of "Physics" 2nd edition by Cutnel and Johnson, John Wiley Publishers, 1992. The liquefied tissue is then transported from the surgical site by a vacuum aspiration system. These devices have two major disadvantages: they are very expensive; and more importantly, due to the high rate of oscillation, all tissue that comes in contact with the device is indiscriminately liquefied and removed by aspiration. The latter shortcoming is particularly troublesome when blood vessels within the targeted tissue need to be preserved. U.S. Pat. No. 4,274,414 to Johnson et al. discloses a system for removing undesired tissue present, for example, in arthroscopic surgery. In the system of Johnson et al., a small caliber tube having a side fenestration near the tip is inserted into the knee joint. A rapidly rotating blade within the tube removes tissue brought in lateral contact with the fenestration, permitting it to be aspirated through the central lumen of the tube. The blade indiscriminately removes all tissue brought in contact therewith.

U.S. Pat. No. 4,747,406 to Nash and U.S. Pat. No. 4,950,278 to Sachse et al. disclose intravascular or endoscopic rotating cutting blades for removing unwanted tissue, generally comprising atheromatous material. The rotating blades are intended to remove atheromatous material built up along the inner walls of larger arteries without causing damage to the underlying arterial wall. This selective removal of atheromatous material, however, is not a function of selective blade action per se, but rather is due to the design of the device, which provides means to confine the blade action of the operative head to the atheromatous tissue to be removed, keeping it away from contact with the vessel wall.

U. S. Pat. No. 4,024,866 discloses a hydraulic surgical cutter having a suction attachment. A pulsating, high velocity liquid jet is directed onto defective tissue from the lens of an eye to disintegrate the tissue. Liquid entraining the disintegrated tissue is removed from the area by the suction attachment. U.S. Pat. No. 5,154,709 discloses a vacuum hood attachment for an electro-cutting blade, which has a hollow tubular body open at each end and a side opening for connection to a vacuum source. U.S. Pat. No. 4,108,182 discloses a surgical vitreous cutting head which uses a reciprocating blade. Further, U.S. Pat. No. 3,882,872 to Douvas et al. and U.S. Pat. No. 3,906,954 to Baehr et al. disclose the use of rotating blades that macerate tissue with a sharp cutting or shearing blade. Like the devices of Johnson et al., Nash and Sachse et al., all tissue contacted by the blades is indiscriminately removed by the Douvas et al. and Baehr et al. devices.

Rapidly growing, malignant brain tumors are generally of different consistency than normal tissue, the degree of softness generally correlating with the degree of anaplasia or invasiveness. An invasive tumor infiltrates or insinuates amidst surrounding normal tissue. Present methods such as Ultrasonic devices indiscriminately liquefy any tissue brought into contact with the operative head and therefore do not differentiate between malignant brain tissue and adjacent normal structures.

A benign tumor on the other hand tends to grow slowly and is self-contained, often encapsulated. A benign tumor tends to displace rather than invade normal structures which, because of the long time interval, are able to gradually give ground while maintaining function so that the presence of the tumor may not be suspected until after many years of growth. These tumors tend to be tougher in consistency than malignant tumors.

Intracerebral hematomas, while solid in nature after clotting has occurred, generally remain softer in consistency than the surrounding, normal brain tissue.

There presently exists no apparatus for differential removal of tissue, in which a rotating blade at an open end of the apparatus liquefies a selected tissue, such as a tumor or intracerebral hematoma, upon contact therewith and removes it by aspiration, while leaving other tissue, such as blood vessels, intact.

SUMMARY OF THE INVENTION

The present invention provides a method and means for differential removal of tissue, in which tumorous tissue is liquefied and simultaneously aspirated through a small caliber instrument in a highly efficient manner while preserving vital tissue such as blood vessels, and the like. Such a small caliber instrument can be made in varying lengths without practical limitations, thus enabling the neurosurgeon to work in deep fields, a requirement which is frequently present in neurosurgical operations. Liquefication of tissue is accomplished by the rotating action of a battering means. The difference in consistency between pathological, infiltrated tissue and normal tissues results in a difference in feel as well as a change in the character of the liquefied product, thereby allowing the surgeon resecting malignant tissue to recognize the boundary of the tissue to be resected. This is supported by experimental work with the apparatus demonstrating that the battering head can recognize membrane interfaces and vascular structures and thus be used to achieve a differential removal of diseased. unwanted tissue without destroying adjacent vital normal structures.

Generally stated. there is provided a surgical instrument for removing diseased tissue, comprising a tubular housing having open proximal and distal ends. A rotating shaft having proximal and distal ends is disposed within the tubular housing. A battering means having a battering edge is disposed at the distal end of the rotating shaft. Fixed within the tubular housing and disposed concentrically around the rotating shaft are a plurality of bearing means. The bearing means provide a means for reducing friction between the tubular housing and the rotating shaft. Rotational power means associated with the shaft impart rotation thereto. A shaft connecting means is provided for connecting the rotating shaft to the rotational power means. Upon rotation of the shaft, the battering means rotates, causing diseased tissue in contact therewith to be liquefied without adversely affecting the structure and function of non-diseased tissue, such as blood vessels and the like. That is to say. the battering action is selective in that liquefaction of diseased tissue is accomplished without destruction of non-diseased tissue, such as blood vessels, which are preserved intact and continue to function without adverse effect. By acting differently on tissues of different consistency, the battering action permits the surgeon to selectively liquefy diseased tissue without collateral destruction of non-diseased tissue, which is left intact and functional. The invention further provides means for vacuum aspiration of the liquefied tissue.

Further, the invention provides a process for differentially removing diseased tissue. such as tumors and other abnormal tissue, in the presence of non-diseased tissue which is generally of different consistency, comprising the steps of: contacting the diseased and non-diseased tissue with an edge of a paddle moving with rotational velocity, the edge being dull and the velocity being sufficient to batter the diseased tissue into a liquid; and removing the liquefied tissue by vacuum aspiration. Optionally, the invention includes other parallel channels for irrigation, optical and/or ultra sonographic monitoring.

Ultrasonic powered neurosurgical devices presently in use require relatively large and cumbersome power sources in the operating room to drive the power tips of the devices. Such devices are expensive. typically costing upwards of $30,000 to $40,000, and their power tips are somewhat bulky and clumsy to use. None of them effects differential removal of tissue in contact with the power tip. The surgical instrument of our invention is inexpensive, more maneuverable, and much more efficient than those devices heretofore available; and operates to differentially separate and selectively remove diseased tissue from non-diseased tissue within the power tip.

BRIEF DESCRIPTION OF THE DRAWINGS

The invention will be more fully understood and further advantages will become apparent when reference is made to the following detailed description of the preferred embodiment of the invention and the accompanying drawings, in which.

DESCRIPTION OF THE PREFERRED EMBODIMENTS

Rapidly growing tumors tend to be of different consistency than normal tissue, the degree of softness generally correlating with the degree of anaplasia or invasiveness. An invasive tumor infiltrates or insinuates amidst surrounding normal tissue.

A benign tumor on the other hand tends to grow slowly and is self-contained, often as a distinct unit. A benign tumor therefore tends to displace normal structures which, because of the long time interval, are able to give ground so that the presence of the tumor may not be suspected until after many years of growth. These tumors tend to be different in consistency than malignant tumors and intracerebral hematomas. Present methods such as Ultrasonic Devices remove any tissue brought into contact with the head and do not differentiate between tumor tissue and normal tissue.

It is a well known principle of physics, (see, for example, "Physics," pages 153–155, by Giancolli, Prentice Hall) that the change in momentum of an object is equal to the product of force applied and time of application of the force, or $P2-P1=F \cdot t$, where P, F, t are momentum, force, and time respectively. This can be seen when catching a hard ball without a glove. In order to reduce the force and therefore the sting, the catcher moves the hands back with the ball in order to increase the time of impact and therefore reduce the force and its subsequent sting. In the same manner, a rotating blade, when impacting tissue undergoes a change in momentum. If the blade has a high rotation speed the time of contact with a specific piece of tissue is short and therefore the force of impact is high and tissue is easily destroyed. Conversely, if the blade has a low rotation speed the time of contact with a specific piece of tissue is long and therefore the force of impact is low destroying only soft tissue. Similarly, rounding or beveling the blade edge would also effectively increase the time of impact, reducing the force of impact. As used herein, the term "low rotational speed" means a rotational speed at which the impact frequency is low in comparison to the frequency of impact of the Ultrasonic Device.

Figure 1:
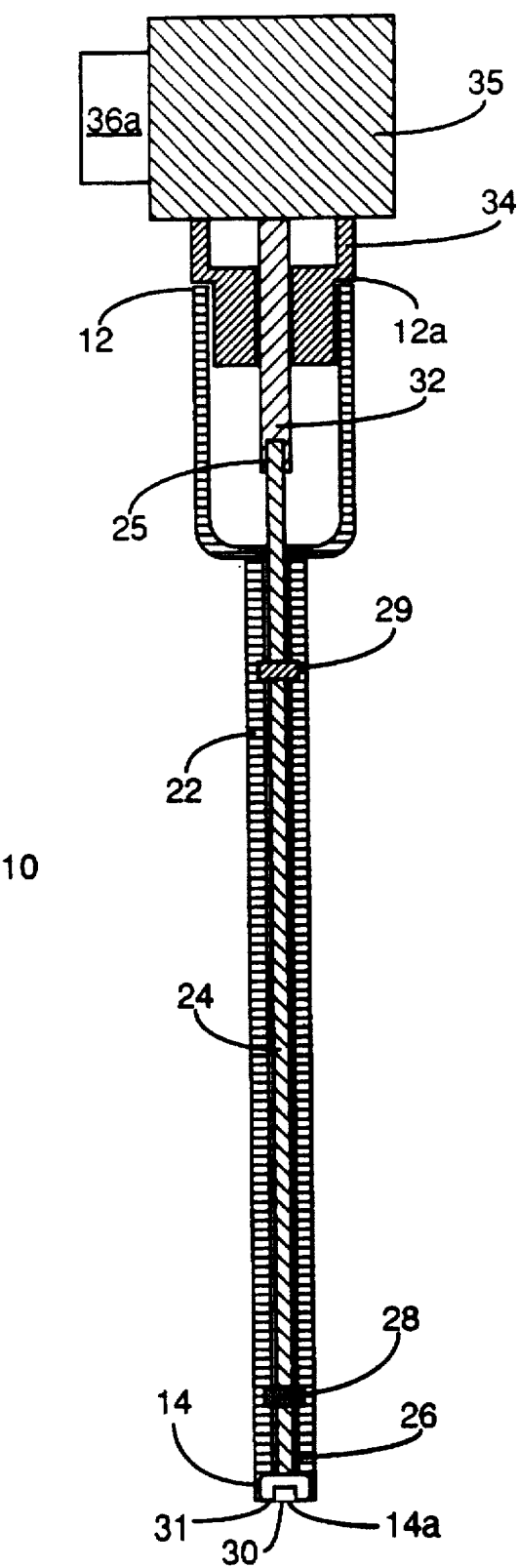
FIG. 1 is a longitudinal cross-sectional view of an instrument for differential removal of tissue in accordance with the present invention.
Figure 2:
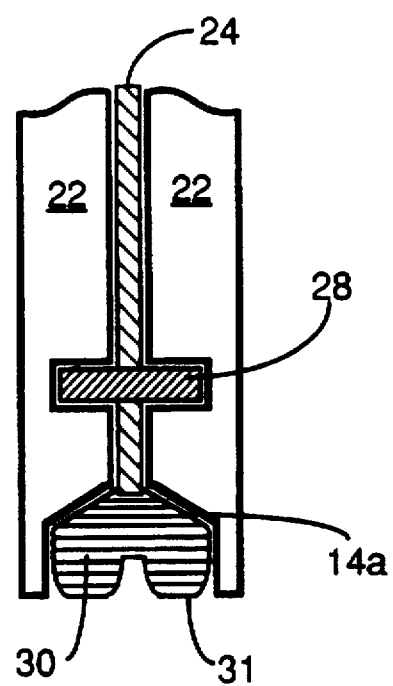
FIG. 2 is an expanded longitudinal cross-sectional view of a portion of the instrument with a recessed paddle.
Figure 2A:
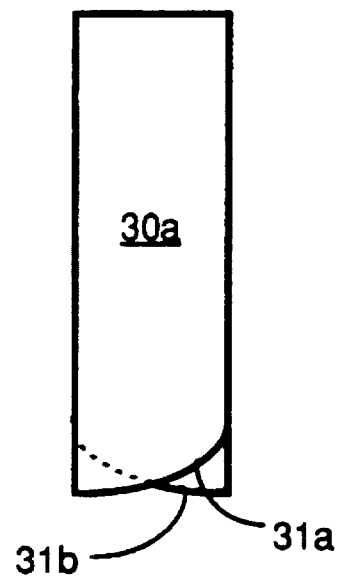
FIG. 2A is a profile view of a paddle provided with a sloped battering edge.

Referring to FIGS. 1 and 2 of the drawings, there is shown an improved instrument 10 for differential removal of tissue. The instrument 10 has tubular housing 22 with an opening 12a at proximal end 12 and an opening 14a at distal end 14. Within tubular housing 22 is a shaft 24 which has proximal end 25 and distal end 26. Shaft 24 is supported within tubular housing 22 by rotary bearings within bearing means 28 and 29. Attached to the distal end 26 of shaft 24 is a battering means, shown in FIG. 1 as paddle 30. Paddle 30 is a dull blade, preferably comprised of stainless steel and having nominal thickness between 0.1 mm and 1 mm. Preferably, battering edge 31 of paddle 30 is approximately flush with the distal end 14 of tubular housing 22. Proximal end 25 of shaft 24 is keyed to fit within power driver 32. Preferably, the inside of proximal end 12 of tubular housing 22 is threaded to connector 34 holding power driver 32 in place. A rotary power means 35, such as an electric motor, or pneumatic or hydraulic rotor is used to rotate power driver 32 and in turn rotate rotary shaft 24. Paddle 30 batters tumorous tissue into a liquid while leaving tough and resilient tissue, such as blood vessels, intact. The rotational velocity of the battering means will vary depending on the type of diseased and non-diseased tissue present in the region appointed for contact by the battering means, the fraction of diseased to non-diseased tissue present in that region, the size and weight of paddle 30 and the dullness of its battering edge 31. As used herein, the term "dull" means that the battering edge is square, beveled, or rounded, as opposed to a sharp, pointed edge which would be used to effect a shearing action upon contact with tissue. The rounded configuration of the battering edges 31a and 31b depicted by FIGS. 2A and 2B is defined by a radius of curvature ranging from about 0.01 millimeters to 1 millimeters, and preferably from about 0.05 millimeters to 0.5 millimeters.

For occasions wherein blood vessels and other non-diseased tissue of similar toughness are to be preserved, the rpm of the battering means should range from about 10,000 to 30,000. In certain instances when all tissue encountered is to be removed, such as typically found with benign tumors, an rpm in excess of 150,000 may be desirable.

Preferably, as shown in FIG. 1, rotational power means 35 is operable at variable speed. The rotation speed of rotational power means 35 is controlled by a switch 36a. Preferably the rotational power means 35 is operable between a low setting of 10,000 and a high setting of 200,000 rpm. Switch 36a is potentiometer allowing continuously variable speeds, or alternatively, switch 36a has at least a high and low speed setting.

Figure 2B:
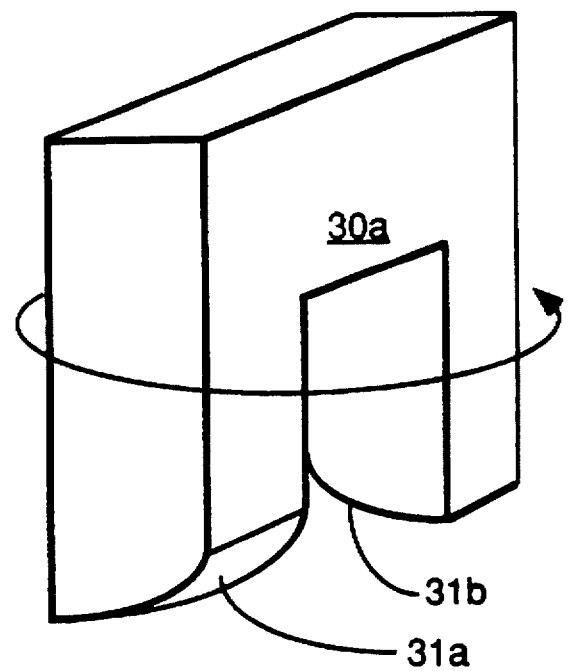
FIG. 2B is a perspective view of a paddle of FIG. 2A provided with a sloped battering edge.
Figure 3:
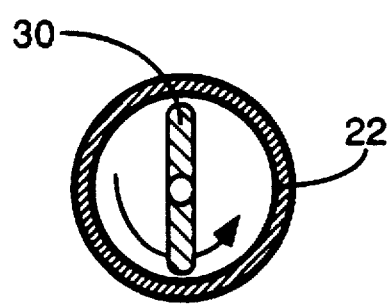
FIG. 3 is a transverse view of the distal end of the instrument of FIG. 1.
Figure 4:
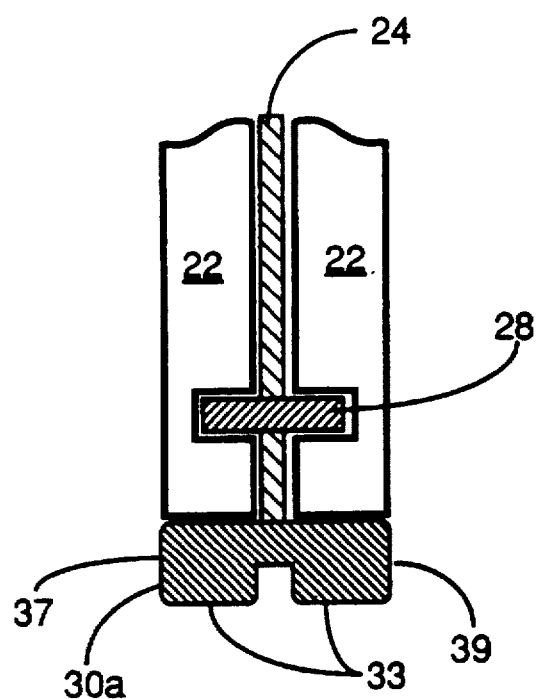
FIG. 4 is an expanded cross-sectional view of a portion of the instrument with a protruding paddle.

Preferably, as shown in FIG. 2B, paddle 30 is nearly "U"-shaped or rectangular in shape and battering edge 31 is flush with the distal end 14 of tubular housing 22. Alternatively, the paddle 30a has a broad continuously sloping edges 31a and 31b as shown in FIGS. 2A and 2B. The arrow in FIG. 2B shows the direction of rotation. FIG. 3 shows the rotation of paddle 30 in distal end 14 of tubular housing 22. Alternatively, as shown in FIG. 4, the battering means represented as paddle 30a protrudes past tubular housing 22. Paddle 30a is provided with battering edges 33, 37, and 39. As another alternative, the battering means takes the shape of a flat or tapered paddle, or a multiple arm paddle.

Figure 5:
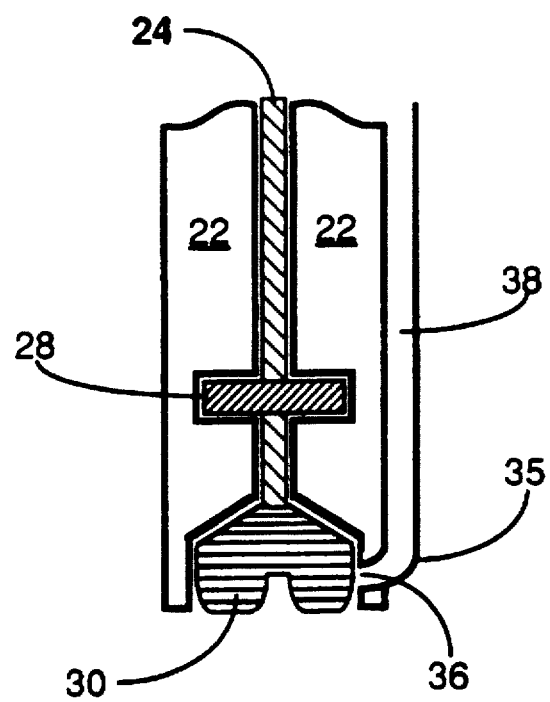
FIG. 5 is an expanded cross-sectional view of the instrument provided with a vacuum aspirator tube.
Figure 6:
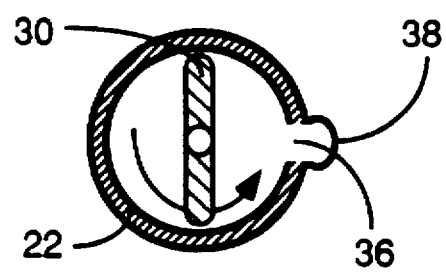
FIG. 6 is an transverse cross-sectional view of the distal end of the instrument provided with a vacuum aspirator tube through the level of connecting port with central lumen.
Figure 7:
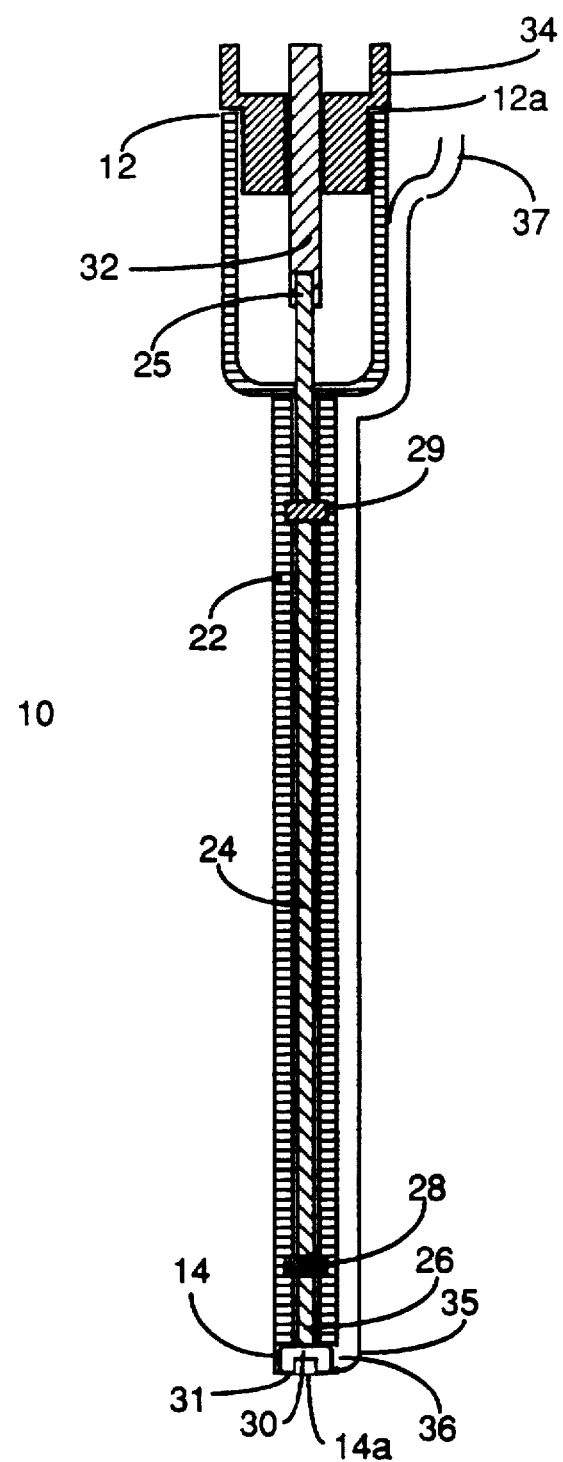
FIG. 7 is a longitudinal cross-sectional view of the instrument provided with a vacuum aspirator tube.

Preferably, as shown in FIGS. 5, 6, and 7, instrument 10 is provided with vacuum aspirator channel or tube 38 disposed along the length of tubular housing 22. A first end 35 of vacuum aspirator tube 38 enters the side wall of the distal end 14 of tubular housing 22 at port 36. A vacuum source is connected to a second end 37 of vacuum aspirator tube 38 near proximal end 12 tubular housing 22. Alternatively, shaft 24 is non-circular (e.g., rectangular or triangular) in shape providing a space between the shaft 24 and the inside of said tubular housing 22; the space, in turn, providing a channel for vacuum aspiration. FIG. 6 is a cross-sectional view at the level of entry port connecting aspiration tube 38 with the central channel. Optionally, instrument 10 is provided with an irrigation tube, similar to vacuum aspiration tube 38, for carrying irrigating fluid to the diseased tissue. As a further option, instrument 10 is provided with a channel or tube for carrying means for transmitting ultrasonographic signal, such as Color Doppler. As a still further option, instrument 10 is provided with a channel or tube disposed along the length of the tubular housing, for carrying optical fibers transmitting light to, and an image from the diseased tissue.

The following example is presented to provide a more complete understanding of the invention. The specific techniques, conditions, materials and reported data set forth to illustrate the principles and practice of the invention are exemplary and should not be construed as limiting the scope of the invention.

EXAMPLE 1

An instrument with a vacuum aspirator tube was fabricated having an overall length of 13 cm, a diameter of 5 mm at the distal end and 1 cm at the proximal end. A commercial Dremel tool was used as the power source. The tool is an electric motor with rotational speeds up to 25,000 RPM. The instrument was tested on three types of tissue purchased at a local market: heart muscle, liver, and brain. Animal brain tissue closely mimics human brain tissue in texture and response. Heart muscle closely simulates firm, resistant brain tumor, such as benign meningioma. Liver falls between brain and heart tissue in firmness or resistance, approximating the response of neuroma. The relatively high vascularity of liver tissue permits assessment of the vessel-sparing action of this device on other, non-neurological tissues.

The instrument was linked to a vacuum source and the cutting tip was brought into contact with each of the test tissues. In each case, pressure from the battering tip caused the tissue in contact to erode or "melt away" in a controlled, well-defined manner, gradually resulting in a cavity of desired shape and size, the liquefied contents being aspirated through the vacuum aspiration tube and thus removed from the site.

EXAMPLE 2

The present invention was further tested on a fourth specimen of animal tissue, placenta, characterized by a high degree of vascularity. The placental tissue was liquefied and aspirated while simultaneously preserving the network of blood vessels overlying the tissue.

In operation, an area overlying a tumor or diseased tissue is surgically exposed and prepared and hemostasis is obtained by conventional means such as electrocautery. The instrument 10 is joined to power driver 32 and the vacuum aspirator tube 38 is attached for vacuum drainage. The distal end 14 is brought in contact with the diseased tissue to be removed. Power is applied and the rotary action of paddle 30 fluidizes the subject tissue, which is thereafter removed by being aspirated into vacuum aspirator tube 38.

Having thus described the invention in rather full detail, it will be understood that such detail need not be strictly adhered to but that further changes and modifications may suggest themselves to one skilled in the art all falling within the scope of the invention as defined by the subjoined claims.

What is claimed is:

1. A surgical instrument for removing diseased tissue in the presence of non-diseased tissue, comprising:

(a) a tubular housing having open proximal and distal ends;

(b) a rotating shaft having proximal and distal ends, said rotating shaft being disposed within said tubular housing;

(c) a rotational power means;

(d) a shaft connecting means for attaching said rotating shaft to said rotational power means; and (e) a battering means having a battering edge disposed at said distal end of said rotating shaft and contained within said housing so that said battering edge is approximately flush with the distal end of said tubular housing, said distal end being operative to push normal living cellular tissue away from said battering means, to permit tissue walls to be simultaneously cleaned by said battering edges, and said battering means being operative, upon rotation at a velocity ranging from about 10,000 to 30,000 rpm, to liquefy diseased tissue while simultaneously preserving the structure and function of non-diseased tissue.

2. A surgical instrument as recited in claim 1, further comprising a vacuum aspiration tube for removing said liquefied diseased tissue, said vacuum aspiration tube being connected to said distal end of said tubular housing and in communication with said distal end of said tubular housing and a vacuum source.

3. A surgical instrument as recited in claim 2, further comprising an irrigation tube disposed along the length of said tubular housing, for carrying irrigating fluid to said diseased tissue.

4. A surgical instrument as recited in claim 1, further comprising a channel disposed along the length of said tubular housing, for carrying optical fibers transmitting light to and from said diseased tissue.

5. A surgical instrument as recited in claim 1, wherein said rotating shaft has a cross-section providing a space between said shaft and the inside of said tubular housing, said space providing a channel for vacuum aspiration.

6. A surgical instrument as recited in claim 1, further comprising a plurality of bearing means fixed within said tubular housing and concentrically disposed around said rotating shaft, said bearing means providing means for reducing friction between said tubular housing and said rotating shaft.

7. A surgical instrument for removing diseased tissue in the presence of non-diseased tissue, comprising:

(a) a tubular housing having open proximal and distal ends;

(b) a rotating shaft having proximal and distal ends, said rotating shaft being disposed within said tubular housing;

(c) a rotational power means, having a high and low speed setting;

(d) a shaft connecting means for attaching said rotating shaft to said rotational power means; and (e) a battering means having a battering edge disposed at said distal end of said rotating shaft to provide a battering action and contained within said housing so that said battering edge is approximately flush with the distal end of said tubular housing, said distal end being operable to limit the action of said battering means and to move normal tissue away while the walls of said tissue are being cleaned;

whereby when said variable speed rotational power means is set to a velocity in excess of 150,000 rpm, said battering means is operative to liquefy all tissue in contact with said battering means, and when said variable speed rotational power means is set to a velocity ranging from about 10,000 to 30,000 rpm, said-battering means is operative, upon rotation, to liquefy diseased tissue without liquefying or adversely affecting the structure and function of non-diseased tissue.

* * * * *